United States Patent
Shi et al.

(10) Patent No.: US 8,642,030 B2
(45) Date of Patent: Feb. 4, 2014

(54) COMPOSITIONS CONTAINING COENZYME Q-10 AND DIHYDROLIPOIC ACID

(75) Inventors: Jingang Shi, Beijing (CN); Chenghai Zhao, Beijing (CN); Wenxian Pan, Beijing (CN); Yunlong Feng, Tianjin (CN)

(73) Assignee: EPC Europe GmbH, Hamburg (DE)

( * ) Notice: Subject to any disclaimer, the term of this patent is extended or adjusted under 35 U.S.C. 154(b) by 1118 days.

(21) Appl. No.: 11/843,935

(22) Filed: Aug. 23, 2007

(65) Prior Publication Data

US 2008/0152706 A1 Jun. 26, 2008

Related U.S. Application Data

(60) Provisional application No. 60/886,395, filed on Jan. 24, 2007.

(30) Foreign Application Priority Data

Aug. 25, 2006 (AT) ................................ A 1422/2006

(51) Int. Cl.
*A61K 38/43* (2006.01)

(52) U.S. Cl.
USPC ...................................................... 424/94.1

(58) Field of Classification Search
USPC ...................................................... 424/94.1
See application file for complete search history.

(56) References Cited

U.S. PATENT DOCUMENTS

| | | | |
|---|---|---|---|
| 6,184,255 B1 | 2/2001 | Mae et al. | |
| 6,300,377 B1 | 10/2001 | Chopra | |
| 6,616,942 B1 | 9/2003 | Udell | |
| 6,623,734 B2 | 9/2003 | Udell et al. | |
| 6,740,338 B1 | 5/2004 | Chopra | |
| 6,806,259 B2 | 10/2004 | Udell et al. | |
| 2002/0147353 A1 | 10/2002 | Van Der Vijgh et al. | |
| 2006/0073131 A1 | 4/2006 | Fujii et al. | |

FOREIGN PATENT DOCUMENTS

| | | | |
|---|---|---|---|
| EP | 1897539 A1 | 3/2008 | |
| JP | 2005-232880 | 12/2005 | |
| WO | 2001052822 A1 | 7/2001 | |
| WO | WO 01/52822 A1 * | 7/2001 | ............. A61K 9/48 |
| WO | 2002017879 A1 | 3/2002 | |

OTHER PUBLICATIONS

Database WPI Week 200604 Thomson Scientific, London, GB; AN 2006-033542; XP002486677 & JP 2005 232880 A (ITO Co. Ltd.) Dec. 15, 2005); abstract.

A. Kozlov et al., Dihydrolipoic Acid Maintains Ubiquinone in the Antioxidant Form by Two-Electron Reduction of Ubiquinone and One-Electron Reduction of Ubisemiquinone, Archives of Biochemistry and Biophysics 363 (1999), pp. 148-154.

J. Maguire et al., Succinate-Ubiquinone Reductase Linked Recycling of Alpha-Tocopherol in Reconstituted Systems and Mitochondira: Requirement for Reduced Ubgiquinone, Archives of Biochemistry and Biophysics 292 (1992), pp. 47-53.

K. Hosoe et al., Study on Safety and Bioavailability of Ubiquinol after single and 4-Week Multiple Oral Administration to Healthy Volunteers, Regulatory Toxicology and Pharmacology 47 (2007), pp. 19-28.

* cited by examiner

*Primary Examiner* — Thane Underdahl

(74) *Attorney, Agent, or Firm* — Fulbright & Jaworski, LLP; Scott D. Rothenberger

(57) ABSTRACT

The invention describes compositions, including soft gelatin capsules, that include dihydrolipoic acid and the reduced form of coenzyme $Q_n$, wherein the dihydrolipoic acid acts as a reducing agent for the coenzyme $Q_n$ and also, optionally, as a solvent.

3 Claims, 2 Drawing Sheets

COMPOSITIONS CONTAINING COENZYME Q-10 AND DIHYDROLIPOIC ACID

CROSS REFERENCE TO RELATED APPLICATIONS

This application claims priority to Austrian patent application A1422/2006, filed Aug. 25, 2006 and U.S. Provisional application 60/886,395, filed Jan. 24, 2007, entitled "Compositions Containing Coenzyme Q-10 and Dihydrolipoic Acid", the contents of which are incorporated herein in their entirety.

FIELD OF THE INVENTION

The invention relates generally unique combinations of a reduced form of coenzyme Q-10 (CoQ10). CoQ10 is reduced to ubiquinol in the presence of dihydrolipoic acid (DHLA), where DHLA serves as not only the reducing agent but also as a carrier.

BACKGROUND OF THE INVENTION

CoQ-10 (coenzyme Q10) is a fat-soluble quinone, a benzoquinone that is structurally similar to vitamin K and commonly known as ubiquinone. CoQ-10 is found in most living organisms, and is essential for the production of cellular energy. CoQ-10 (2,3 dimethyl-5 methyl-6-decaprenyl benzoquinone) is an endogenous antioxidant found in small amounts in meats and seafood. Although CoQ-10 is found in all human cells, the highest concentrations of CoQ-10 occur in the heart, liver, kidneys, and pancreas. It is found naturally in the organs of many mammalian species.

CoQ-10 is an important nutrient because it lies within the membrane of a cell organelle called the mitochondria. Mitochondria are known as the "power house" of the cell because of their ability to produce cellular energy, or ATP, by shuttling protons derived from nutrient breakdown through the process of aerobic (oxygen) metabolism. CoQ-10 also has a secondary role as an antioxidant. CoQ-10, due to the involvement in ATP synthesis, affects the function of almost all cells in the body, making it essential for the health of all human tissues and organs. CoQ-10 particularly effects the cells that are the most metabolically active: heart, immune system, gingiva, and gastric mucosa CoQ-10 is sparingly soluble in most hydrophilic solvents such as water. Therefore, CoQ-10 is often administered in a powdered form, as in a tablet or as a suspension. However, delivery of CoQ-10 by these methods limits the bioavailability of the material to the individual.

Several clinical trials have shown CoQ-10 to be effective in supporting blood pressure and cholesterol levels. Furthermore, CoQ-10 has also been shown to improve cardiovascular health. CoQ-10 has been implicated as being an essential component in thwarting various diseases such as certain types of cancers. These facts lead many to believe that CoQ-10 supplementation is vital to an individual's well being.

Reduced benzoquinones are known to be effective reductants for oxygen or lipid radicals. Some studies have shown that reduced CoQ-10 (ubiquinol) is an effective antioxidant. In fact, reduced CoQ-10 now appears to function as part of a complex chain of antioxidant activity. Apparently, reduced CoQ-10 plays a role in the reduction of radicals of alpha-tocopherol and ascorbate formed when these antioxidants are oxidized by oxygen or carboxyl radicals present in physiological systems. There are no known enzymes for direct reduction of a tocopheryl radical or an external ascorbate radical, but there are enzymes in all membranes that can reduce CoQ-10 and thus reduced CoQ-10 can subsequently reduce the tocopheryl or ascorbate radicals to provide tocopherol or ascorbate. Without the support of enzymes to reduce CoQ-10, the reduced coQ-10 would not be a very effective antioxidant as the semiquinone formed by interaction with lipid or oxygen radicals is readily autooxidized with formation of a superoxide radical.

Therefore, a need exists for methods and compositions that provide reduced CoQ-10 in a form that can be assimilated and retains antioxidant activity.

BRIEF SUMMARY OF THE INVENTION

The present invention surprisingly provides solutions of coenzyme Q-10 (CoQ-10) and reduced CoQ-10 with dihydrolipoic acid (DHLA). Interestingly, when at least a molar amount of DHLA is combined with a molar equivalent of CoQ-10, the oxidized form of CoQ-10 is reduced to the reduced form of CoQ-10. Generally, greater than 90% of the oxidized form of CoQ-10 is converted to the reduced form of CoQ-10 and in particular greater than 95% conversion occurs, to a point where essentially no oxidized CoQ-10 remains. Excess DHLA serves then as a solvent carrier and helps to stabilize the reduced CoQ-10, making shelf stable for extended periods of time.

In one aspect, the present invention provides a reduced coenzyme Q-10 (CoQ-10) composition that includes a sufficient amount of dihydrolipoic acid (DHLA) to reduce CoQ-10 to a reduced form of CoQ-10 in greater than 95% by weight. In certain embodiments, the composition does not include an ethanolic solution containing 8% water.

In another aspect, the present invention provides reduced coenzyme Q-10 (CoQ-10) compositions that consist essentially of a sufficient amount of dihydrolipoic acid (DHLA) to reduce CoQ-10 to a reduced form of CoQ-10 in greater than 95% by weight.

In still another aspect, the present invention provides a soft gelatin capsule that encapsulates a reduced coenzyme Q-10 (CoQ-10) composition. The reduced CoQ-10 composition includes a sufficient amount of dihydrolipoic acid (DHLA) to reduce CoQ-10 to a reduced form of CoQ-10 in greater than 95% by weight.

In yet another aspect, the present invention provides a soft gelatin capsule that encapsulates a reduced coenzyme Q-10 (CoQ-10) composition that, consists essentially of: a sufficient amount of dihydrolipoic acid (DHLA) to reduce CoQ-10 to a reduced form of CoQ-10 in greater than 95% by weight.

The compositions and soft gelatin capsules can further include various carriers and additives, such as suitable antioxidants and/or vitamins.

The present invention also provides a method to prepare solutions of reduced CoQ-10.

The present invention further provides methods to treat various conditions associated with decreased levels of CoQ-10, such as mitochondrial related diseases and disorders, Parkinson's disease, Prater-Willey syndrome, migraine headaches or headaches by administering to the individual in need thereof, an effective amount of any of the compositions disclosed herein.

In still another aspect, the present invention also provides packaged neutraceuticals that are disclosed herein.

While multiple embodiments are disclosed, still other embodiments of the present invention will become apparent to those skilled in the art from the following detailed description. As will be apparent, the invention is capable of modifi-

DETAILED DESCRIPTION

Figure 1:
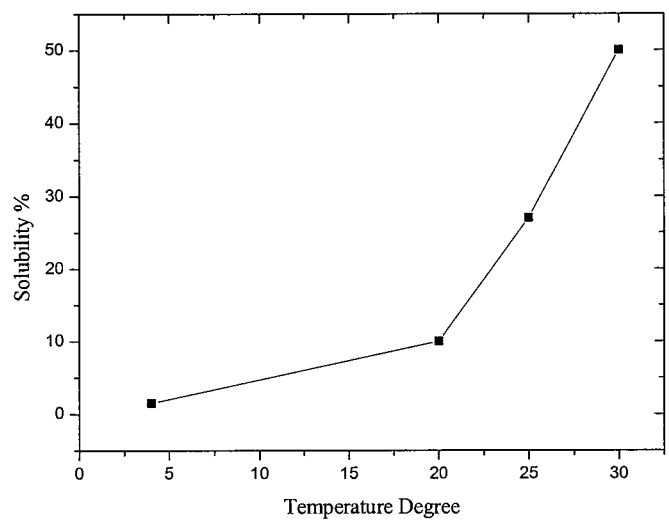
FIG. 1 exhibits the solubility of CoQ-10 at various temperatures in DHLA.

The present invention surprisingly provides solutions of coenzyme Q-10 (CoQ-10) and reduced CoQ-10 with dihydrolipoic acid (DHLA). Interestingly, when at least a molar amount of DHLA is combined with a molar equivalent of CoQ-10, the oxidized form of CoQ-10 is reduced to the reduced form of CoQ-10.

Generally, greater than 90% of the oxidized form of CoQ-10 is converted to the reduced form of CoQ-10 and in particular greater than 95%, more particularly, 96%, still more particularly, 97%, more particularly 98%, still more particularly, 99% conversion occurs, to a point where essentially no oxidized CoQ-10 remains. Excess DHLA serves then as a solvent carrier and helps to stabilize the reduced CoQ-10, making shelf stable for extended periods of time.

In one aspect, the present invention provides a reduced coenzyme Q-10 (CoQ-10) composition that includes a sufficient amount of dihydrolipoic acid (DHLA) to reduce CoQ-10 to a reduced form of CoQ-10 in greater than 95% by weight. In certain embodiments, the composition does not include an ethanolic solution containing 8% water.

In the specification and in the claims, the terms "including" and "comprising" are open-ended terms and should be interpreted to mean "including, but not limited to . . . ." These terms encompass the more restrictive terms "consisting essentially of" and "consisting of."

Dihydrolipoic acid (DHLA) is a constituent of cellular metabolism. DHLA has two thiol residues that make is susceptible to radical species, thus provides antioxidant functionality to the biomolecule. Oxidation reduction (redox reactions) involves the transfer of an electron from a donor to an acceptor. When the donor loses an electron, it is transformed from its reduced form to its oxidized form. When an acceptor gains an electron, it changes from its oxidized form to its reduced form. Together, the oxidized and reduced forms of a redox component, such as lipoic acid and DHLA or CoQ-10 (ubiquinone) and reduced CoQ-10 (ubiquinol) are called "redox couples."

Dihydrolipoic acid is the reduced (has electrons added) form of lipoic acid (thioctic acid). When DHLA is oxidized (has electrons removed) lipoic acid is produced. It should be understood that DHLA can be either the R or S enantiomer or it can be racemic. Likewise, lipoic acid can also be enantiomerically pure or racemic.

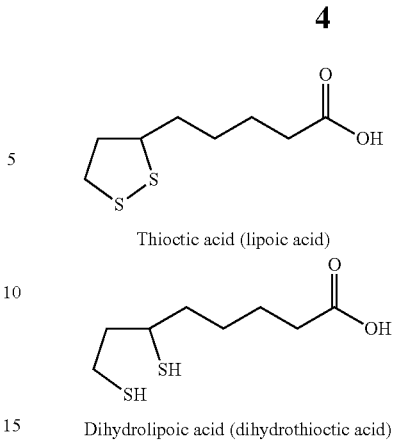

Thioctic acid (lipoic acid)

Dihydrolipoic acid (dihydrothioctic acid)

Likewise, ubiquinol is the reduced (has electrons added) form of ubiquinone (CoQ-10). When ubiquinol is oxidized (has electrons removed), ubiquinone is produced.

Surprisingly, it has been found by the present invention that at pH ranges of below 7, the present invention did not provide any indication of a radical formation as noted by UV spectrometry. Not to be limited by theory, it is believed that a "2 electron transfer" reaction takes place under these conditions. This seems also logical for, as at the pH of the reaction DHLA is not susceptible to radical formation, which would be a prerequisite for a radical reaction.

This results are surprising in that at pH values of 7 or greater, typically lipoic acid donates an electron to DHLA, and the DHLA reacts with a free radical and is then oxidized back into lipoic acid, and the lipoic acid is then reduced using cellular reducing equivalents (NADH or NADPH) back into DHLA thus continuing the redox cycle. As the two forms swap electrons, they rapidly convert. Many of the properties of lipoic acid depend on this ability to rapidly swap electrons. In combination with this redox pair, DHLA can donate an electron to other oxidized species, such as CoQ-10, thus reducing the CoQ-10 to ubiquinol and oxidizing the DHLA to lipoic acid.

The term "coenzyme Q" or "ubiquinone" (CoQ-10) is used throughout the present specification to describe a group of lipid soluble benzoquinones involved in electron transport in mitochondrial preparations, i.e., in the oxidation of succinate or reduced nicotine adenine dinucleotide (NADH) via the cytochrome system. The compounds can be described as: coenzyme $Q_n$ where n is 1-12 or ubiquinone (x) in which x designates the total number of carbon atoms in the side chain and can be any multiple of 5. Differences in properties are due to the difference in the chain length. In particular, ubiquinone for use in the present invention is the reduced form of coenzyme Q10, known as ubiquinol. Therefore, the term CoQ-10 includes all variations where n is from 1 to 12. Likewise, reduced CoQ-10 also includes all variation where n is from 1 to 12.

The term "ubiquinol" is used throughout the specification to describe the reduced form of coenzyme $Q_n$ that is used as the active agent in compositions according to the present invention. In ubiquinol, the quinone ring of coenzyme $Q_n$ is reduced such that the structure of the compound appears as set forth below. In one aspect, ubiquinol, n is preferably 10 and is derived from coenzyme $Q_{10}$. The amount of ubiquinol which is included in compositions according to the present invention ranges from about 0.1% to about 50% by weight of the final composition which is encapsulated in a soft gelatin capsule, more preferably about 0.5% to about 10% by weight, even more preferably about 1% to about 5% by weight. The amount of ubiquinol which is included in compositions to be encapsulated ranges from about 0.1 to about 10.0 times, more preferably about 1 to about 3 times the amount (in weight percent) of the lipid soluble reducing agent which is included in compositions according to the present invention.

It should be understood, that throughout this specification, reference to CoQ-10 and reduced CoQ-10 refers to all possible derivatives where n is as detailed above.

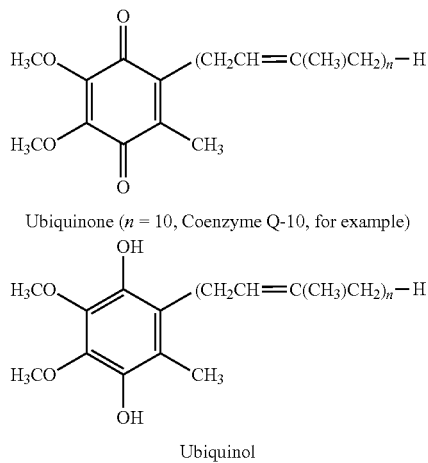

Ubiquinone (n = 10, Coenzyme Q-10, for example)

Ubiquinol

While not being limited by way of theory, it is believed that effective concentrations of DHLA convert substantially all ubiquinone to ubiquinol. In other embodiments, effective concentrations of DHLA also help prevent ubiquinol from being oxidized to ubiquinone, or alternatively reduce any ubiquinone, which has been oxidized from ubiquinol during storage of the compositions according to the present invention.

The concentration of coenzyme Q10 in DHLA can range from about 1% to about 33% (w/w), in particular, from about 3% to about 22%, most particularly from about 8% to about 15% (w/w). At higher concentrations, especially at 25% or more, there is a tendency of COQ10 to crystallize. However, it has been found possible to produce solutions of CoQ10 in DHLA with a weight ratio of, for example, about 33% CoQ10 to about 67% DHLA or even 2 weight parts of CoQ10 to 1 weight part of DHLA, although the reaction time to produce such solutions may be in the range of several weeks.

Solutions containing a weight ratio of CoQ10 to DHLA of 2:1 or more tend to crystallize and to be present in solid form at room temperature.

The compositions according to the present invention can be present in liquid form. Otherwise, the composition can, at room temperature, be present as a gel or as a solid, dependent on the CoQ10-concentration, but may become liquid at body temperature (37° C.). If the concentration of CoQ10 in a solution in DHLA is below 22%, a solid mixture will become a clear solution within 6 minutes at a temperature of 37° C.

In one aspect, the dissolution step is carried out at a pH-value of below 5. In one embodiment, the reaction medium generally does not include any solvent other than DHLA and no agent, which would adjust the pH to a value of 5 or higher.

The products according to the present invention are especially useful due to the fact that they are able to provide effective doses of both reduced CoQ10 and DHLA/Lipoic Acid in one single product. Typically CoQ10 is dosed between about 10 to 30 mg and Lipoic Acid is dosed between 50 to 200 mg. Hence, e.g., 100 to 150 mg of a solution according to the present invention may deliver both CoQ10 and DHLA/Lipoic Acid at an effective concentration.

Suitable carriers include but are not limited to, for example, fatty acids, esters and salts thereof, that can be derived from any source, including, without limitation, natural or synthetic oils, fats, waxes or combinations thereof. Moreover, the fatty acids can be derived, without limitation, from non-hydrogenated oils, partially hydrogenated oils, fully hydrogenated oils or combinations thereof. Non-limiting exemplary sources of fatty acids (their esters and salts) include seed oil, fish or marine oil, canola oil, vegetable oil, safflower oil, sunflower oil, nasturtium seed oil; mustard seed oil, olive oil, sesame oil, soybean oil, corn oil, peanut oil, cottonseed oil, rice bran oil, babassu nut oil, palm oil, low erucic rapeseed oil, palm kernel oil, lupine oil, coconut oil, flaxseed oil, evening primrose oil, jojoba, tallow, beef tallow, butter, chicken fat, lard, dairy butterfat, shea butter or combinations thereof.

Specific non-limiting exemplary fish or marine oil sources include shellfish oil, tuna oil, mackerel oil, salmon oil, menhaden, anchovy, herring, trout, sardines or combinations thereof. In particular, the source of the fatty acids is fish or marine oil (DHA or EPA), soybean oil or flaxseed oil. Alternatively or in combination with one of the above identified carriers, beeswax can be used as a suitable carrier, as well as suspending agents such as silica (silicon dioxide).

Specific non-limiting exemplary fish or marine oil sources include shellfish oil, tuna oil, mackerel oil, salmon oil, menhaden, anchovy, herring, trout, sardines or combinations thereof. In particular, the source of the fatty acids is fish or marine oil (DHA or EPA), soybean oil or flaxseed oil. Alternatively or in combination with one of the above identified carriers, beeswax can be used as a suitable carrier, as well as suspending agents such as silica (silicon dioxide).

Additionally, limonene singly, and/or with other cyclic monoterpene containing essential oil(s), such as orange oil (which may contain 95% or more d-limonene) can be included with one or more carriers. Non-limiting examples of d-limonene containing oils include Lavindin, Peppermint, Ginger, Camphor, Geranium, Orange, Lemon, Lavender, Tea Tree, and Rosemary.

The formulations of the invention are considered dietary supplements useful to the increase the amounts of reduced CoQ-10 and/or additional antioxidants in individuals in need thereof.

The formulations of the invention can also be used in cosmetic products.

Alternatively, the formulations of the invention are also considered to be nutraceuticals. The term "nutraceutical" is recognized in the art and is intended to describe specific chemical compounds found in foods that may prevent disease. Reduced CoQ-10 and antioxidants are such compounds.

The formulations of the invention can further include various ingredients to help stabilize, or help promote the bioavailability of the CoQ-10 and/or amino acid(s), or serve as additional nutrients to an individual's diet. Suitable additives can include vitamins and biologically-acceptable minerals. Non-limiting examples of vitamins include vitamin A, B vitamins, vitamin C, vitamin D, vitamin E, vitamin K and folic acid. Non-limiting examples of minerals include iron, calcium, magnesium, potassium, copper, chromium, zinc, molybdenum, iodine, boron, selenium, manganese, derivatives thereof or combinations thereof. These vitamins and minerals may be from any source or combination of sources, without limitation. Non-limiting exemplary B vitamins include, without limitation, thiamine, niacinamide, pyridoxine, riboflavin, cyanocobalamin, biotin, pantothenic acid or combinations thereof.

Vitamin(s), if present, are present in the composition of the invention in an amount ranging from about 5 mg to about 500 mg. More particularly, the vitamin(s) is present in an amount ranging from about 10 mg to about 400 mg. Even more specifically, the vitamin(s) is present from about 250 mg to about 400 mg. Most specifically, the vitamin(s) is present in an amount ranging from about 10 mg to about 50 mg. For example, B vitamins are in usually incorporated in the range of about 1 milligram to about 10 milligrams, i.e., from about 3 micrograms to about 50 micrograms of B12. Folic acid, for example, is generally incorporated in a range of about 50 to about 400 micrograms, biotin is generally incorporated in a range of about 25 to about 700 micrograms and cyanocobalamin is incorporated in a range of about 3 micrograms to about 50 micrograms.

Mineral(s), if present, are present in the composition of the invention in an amount ranging from about 25 mg to about 1000 mg. More particularly, the mineral(s) are present in the composition ranging from about 25 mg to about 500 mg. Even more particularly, the mineral(s) are present in the composition in an amount ranging from about 100 mg to about 600 mg.

Various additives can be incorporated into the present compositions. Optional additives of the present composition include, without limitation, phospholipids, L-carnitine, starches, sugars, fats, antioxidants, amino acids, proteins, flavorings, coloring agents, hydrolyzed starch(es) and derivatives thereof or combinations thereof.

As used herein, the term "phospholipid" is recognized in the art, and refers to phosphatidyl glycerol, phosphatidyl inositol, phosphatidyl serine, phosphatidyl choline, phosphatidyl ethanolamine, as well as phosphatidic acids, ceramides, cerebrosides, sphingomyelins and cardiolipins.

As used herein, the term "antioxidant" is recognized in the art and refers to synthetic or natural substances that prevent or delay the oxidative deterioration of a compound. Exemplary antioxidants include tocopherols, flavonoids, catechins, superoxide dismutase, lecithin, gamma oryzanol; vitamins, such as vitamins A, C (ascorbic acid) and E and beta-carotene; natural components such as camosol, camosic acid and rosmanol found in rosemary and hawthorn extract, proanthocyanidins such as those found in grapeseed or pine bark extract, and green tea extract.

The term "flavonoid" as used herein is recognized in the art and is intended to include those plant pigments found in many foods that are thought to help protect the body from cancer. These include, for example, epi-gallo catechin gallate (EGCG), epi-gallo catechin (EGC) and epi-catechin (EC).

Any dosage form, and combinations thereof, are contemplated by the present invention. Examples of such dosage forms include, without limitation, chewable tablets, elixirs, liquids, solutions, suspensions, emulsions, capsules, soft gelatin capsules, hard gelatin capsules, caplets, lozenges, chewable lozenges, suppositories, creams, topicals, ingestibles, injectables, infusions, health bars, confections, animal feeds, cereals, cereal coatings, and combinations thereof. The preparation of the above dosage forms are well known to persons of ordinary skill in the art.

For example, health bars can be prepared, without limitation, by mixing the formulation plus excipients (e.g., binders, fillers, flavors, colors, etc.) to a plastic mass consistency. The mass is then either extended or molded to form "candy bar" shapes that are then dried or allowed to solidify to form the final product.

Soft gel or soft gelatin capsules can be prepared, for example, without limitation, by dispersing the formulation in an appropriate vehicle (e.g. rice bran oil, DHLA and/or beeswax) to form a high viscosity mixture. This mixture is then encapsulated with a gelatin based film using technology and machinery known to those in the soft gel industry. The industrial units so formed are then dried to constant weight. Typically, the weight of the capsule is between about 100 to about 2500 milligrams and in particular weigh between about 1500 and about 1900 milligrams, and more specifically can weigh between about 1500 and about 2000 milligrams.

For example, when preparing soft gelatin shells, the shell can include between about 20 to 70 percent gelatin, generally a plasticizer and about 5 to about 60% by weight sorbitol. The filling of the soft gelatin capsule is liquid (principally limonene, in combination with rice bran oil and/or beeswax if desired) and can include, apart form the antioxidant actives, a hydrophilic matrix. The hydrophilic matrix, if present, is a polyethylene glycol having an average molecular weight of from about 200 to 1000. Further ingredients are optionally thickening agents. In one embodiment, the hydrophilic matrix includes polyethylene glycol having an average molecular weight of from about 200 to 1000, 5 to 15% glycerol, and 5 to 15% by weight of water. The polyethylene glycol can also be mixed with propylene glycol and/or propylene carbonate.

In another embodiment, the soft gel capsule is prepared from gelatin, glycerine, water and various additives. Typically, the percentage (by weight) of the gelatin is between about 30 and about 50 weight percent, in particular between about 35 and about weight percent and more specifically about 42 weight percent. The formulation includes between about 15 and about 25 weight percent glycerine, more particularly between about 17 and about 23 weight percent and more specifically about 20 weight percent glycerine.

The remaining portion of the capsule is typically water. The amount varies from between about 25 weigh percent and about 40 weight percent, more particularly between about 30 and about 35 weight percent, and more specifically about 35 weight percent. The remainder of the capsule can vary, generally, between about 2 and about 10 weight percent composed of a flavoring agent(s), sugar, coloring agent(s), etc. or combination thereof. After the capsule is processed, the water content of the final capsule is often between about 5 and about 10 weight percent, more particularly 7 and about 12 weight percent, and more specifically between about 9 and about 10 weight percent.

As for the manufacturing, it is contemplated that standard soft shell gelatin capsule manufacturing techniques can be used to prepare the soft-shell product. Examples of useful manufacturing techniques are the plate process, the rotary die process pioneered by R. P. Scherer, the process using the Norton capsule machine, and the Accogel machine and process developed by Lederle. Each of these processes are mature technologies and are all widely available to any one wishing to prepare soft gelatin capsules.

Typically, when a soft gel capsule is prepared, the total weight is between about 250 milligrams and about 2.5 gram in weight, e.g., 400-750 milligrams. Therefore, the total weight of additives, such as vitamins and antioxidants, is between about 80 milligrams and about 2000 milligrams, alternatively, between about 100 milligrams and about 1500 milligrams, and in particular between about 120 milligrams and about 1200 milligrams. In particular, the soft gel capsule typically weighs between about 1000 milligrams and 1300 milligrams, wherein the percentage fill is about 50% of the entire weight of the capsule, i.e., from about 500 to about 650 milligrams fill weight. The fill weight includes the active ingredient(s), solubilizing agents, etc.

Preparation of the soft gel capsules was accomplished by methods well known in the art including, but not limited to those described throughout the specification and in U.S. Pat. Nos. 6,616,942, 6,623,734 and pending U.S. Ser. Nos. 10/035,753 and 09/825,920, the contents of which are incorporated herein by reference in their entirety.

For example, a soft gel capsule can be prepared by mixing a DHLA solution of reduced CoQ-10 to provide a syrupy mixture. The mixture is then encapsulated within a gelatin capsule as described above.

Tablets, capsules, powders and/or solutions can include one or more of excipients, disintegrants, lubricants, binders, colorants, aggregation inhibitors, absorption enhancers, solubilizing agents, stabilizer and the like.

Excipients include, for example, white sugar, lactose, glucose, corn starch, mannitol, crystalline cellulose, calcium phosphate, calcium sulfate and the like.

Disintegrants include, for example, starch, agar, calcium citrate, calcium carbonate, sodium hydrogen carbonate, dextrin, crystalline cellulose, carboxymethylcellulose, tragacanth and the like.

Lubricants include, for example, talc, magnesium stearate, polyethylene glycol, silica, hardened vegetable oils and the like.

Binders include, for example, ethylcellulose, methylcellulose, hydroxypropylmethylcellulose, tragacanth, shellac, gelatin, gum arabic, polyvinylpyrrolidone, polyvinyl alcohol, polyacrylic acid, polymethacrylic acid, sorbitol and the like.

The present invention also provides packaged formulations of reduced CoQ-10 and/or CoQ-10 and DHLA and instructions for use of the tablet, capsule, elixir, etc. Typically, the packaged formulation, in whatever form, is administered to an individual in need thereof that requires an increase in the amount of reduced CoQ-10 in the individual's diet. Typically, the dosage requirement is between about 1 to about 4 dosages a day.

CoQ-10 has been implicated in various biochemical pathways and is suitable for the treatment of cardiovascular conditions, such as those associated with, for example, statin drugs that effect the body's ability to product CoQ-10 naturally. CoQ-10 has also been implicated in various periodontal diseases. Furthermore, CoQ-10 has been implicated in mitochondrial related diseases and disorders, such as the inability to product acetyl coenzyme A, neurological disorders, for example, such as Parkinson's disease and, Prater-Willey syndrome, migraine headaches and headaches.

The following paragraphs enumerated consequently from 1 through 63 provide for various aspects of the present invention. In one embodiment, in a first paragraph (1), the present invention provides a reduced coenzyme Q-10 (CoQ-10) composition, comprising:

a sufficient amount of dihydrolipoic acid (DHLA) to reduce CoQ-10 to a reduced form of CoQ-10 in greater than 95% by weight, provided that the composition does not include an ethanolic solution containing 8% water.

2. The composition of the first paragraph, further comprising a carrier.

3. The composition of the second paragraph, wherein the carrier is DHLA.

4. The composition of the second paragraph, wherein the carrier is a vegetable oil, a fish oil or a combination thereof.

5. The composition of any of paragraphs 1 through 4, further comprising a an antioxidant or an antioxidant enzyme.

6. The composition of paragraph 5, wherein the antioxidant is vitamin E, a vitamin E derivative, vitamin C, a vitamin C derivative, probucol, lycopene, vitamin A, a carotenoid, vitamin B, vitamin B1, a vitamin B derivative, a flavonoid, a polyphenol, glutathione, pyrroloquinoline quinone, Pycnogenol, Flavangenol, selenium, a lipoic acid, a lipoic acid derivative, a carnitine (e.g., L-carnitine) or mixtures thereof.

7. The composition of paragraph 5, wherein the antioxidant enzyme is superoxide dismutase, glutathione peroxidase, glutathione-S-transferase, glutathione reductase, catalase and ascorbic acid peroxidase or mixtures thereof.

8. The composition of any of paragraphs 1 through 7, wherein the pH range of the composition is between about a pH of 6 and a pH of 3.

9. The composition of paragraph 8, wherein the pH range is between about 5.5 and about 3.5.

10. The composition of paragraph 9, wherein the pH range is between about 4 and about 3.5.

11. The composition of paragraph 10, wherein the pH range is between about 3.9 to about 3.8.

12. The composition of any of paragraphs 1 through 11, wherein the reduced form of CoQ-10 is present in an amount of about 98.5% by weight or greater.

13. The composition of any of paragraphs 1 through 11, wherein essentially all of the CoQ-10 is present in the reduced form.

14. A reduced coenzyme Q-10 (CoQ-10) composition, consisting essentially of:

a sufficient amount of dihydrolipoic acid (DHLA) to reduce CoQ-10 to a reduced form of CoQ-10 in greater than 95% by weight.

15. The composition of paragraph 14, wherein the composition does not include an ethanolic solution containing 8% water.

16. The composition of either paragraphs 14 or 15, further comprising a carrier.

17. The composition of paragraph 16, wherein the carrier is DHLA.

18. The composition of paragraph 16, wherein the carrier is a vegetable oil, a fish oil or a combination thereof.

19. The composition of any of paragraphs 14 through 18, further comprising a an antioxidant or an antioxidant enzyme.

20. The composition of paragraph 19, wherein the antioxidant is vitamin E, a vitamin E derivative, vitamin C, a vitamin C derivative, probucol, lycopene, vitamin A, a carotenoid, vitamin B, vitamin B1, a vitamin B derivative, a flavonoid, a polyphenol, glutathione, pyrroloquinoline quinone, Pycnogenol, Flavangenol, selenium, a lipoic acid, a lipoic acid derivative, a carnitine (e.g., L-carnitine) or mixtures thereof.

21. The composition of paragraph 19, wherein the antioxidant enzyme is superoxide dismutase, glutathione peroxidase, glutathione-S-transferase, glutathione reductase, catalase and ascorbic acid peroxidase or mixtures thereof.

22. The composition of any of paragraphs 14 through 21, wherein the pH range of the composition is between about a pH of 6 and a pH of 3.

23. The composition of paragraph 22, wherein the pH range is between about 5.5 and about 3.5.

24. The composition of paragraph 23, wherein the pH range is between about 4 and about 3.5.

25. The composition of paragraph 24, wherein the pH range is between about 3.9 to about 3.8.

26. The composition of any of paragraphs 14 through 25, wherein the reduced form of CoQ-10 is present in an amount of about 98.5% by weight or greater.

27. The composition of any of paragraphs 14 through 25, wherein essentially all of the CoQ-10 is present in the reduced form.

28. A soft gelatin capsule that encapsulates a reduced coenzyme Q-10 (CoQ-10) composition, comprising:
a reduced coenzyme Q-10 (CoQ-10) composition, comprising:
a sufficient amount of dihydrolipoic acid (DHLA) to reduce CoQ-10 to a reduced form of CoQ-10 in greater than 95% by weight; and
a soft gelatin capsule that encapsulates the reduced coenzyme Q-10 (CoQ-10) composition.

29. The soft gelatin capsule of paragraph 16, wherein, the reduced CoQ-10 composition does not include an ethanolic solution that contains 8% water.

30. The soft gelatin capsule of either paragraphs 28 or 29, further comprising a carrier.

31. The soft gelatin capsule of paragraph 30, wherein the carrier is DHLA.

32. The soft gelatin capsule of paragraph 30, wherein the carrier is a vegetable oil, a fish oil or a combination thereof.

33. The soft gelatin capsule of any of paragraphs 28 through 32, further comprising a an antioxidant or an antioxidant enzyme.

34. The soft gelatin capsule of paragraph 33, wherein the antioxidant is vitamin E, a vitamin E derivative, vitamin C, a vitamin C derivative, probucol, lycopene, vitamin A, a carotenoid, vitamin B, vitamin B1, a vitamin B derivative, a flavonoid, a polyphenol, glutathione, pyrroloquinoline quinone, Pycnogenol, Flavangenol, selenium, a lipoic acid, a lipoic acid derivative, a carnitine (e.g., L-camitine) or mixtures thereof.

35. The soft gelatin capsule of paragraph 33, wherein the antioxidant enzyme is superoxide dismutase, glutathione peroxidase, glutathione-S-transferase, glutathione reductase, catalase and ascorbic acid peroxidase or mixtures thereof.

36. The soft gelatin capsule of any of paragraphs 28 through 35, wherein the pH range of the composition is between about a pH of 6 and a pH of 3.

37. The soft gelatin capsule of paragraph 36, wherein the pH range is between about 5.5 and about 3.5.

38. The soft gelatin capsule of paragraph 37, wherein the pH range is between about 4 and about 3.5.

39. The soft gelatin capsule of paragraph 38, wherein the pH range is between about 3.9 to about 3.8.

40. The soft gelatin capsule of any of paragraphs 28 through 39, wherein the reduced form of CoQ-10 is present in an amount of about 98.5% by weight or greater.

41. The soft gelatin capsule of any of paragraphs 28 through 39, wherein essentially all of the CoQ-10 is present in the reduced form.

42. A soft gelatin capsule that encapsulates a reduced coenzyme Q-10 (CoQ-10) composition, consisting essentially of:
a sufficient amount of dihydrolipoic acid (DHLA) to reduce CoQ-10 to a reduced form of CoQ-10 in greater than 95% by weight; and
a soft gelatin capsule that encapsulates the reduced coenzyme Q-10 (CoQ-10) composition.

43. The soft gelatin capsule of paragraph 42, wherein the soft gelatin capsule does not include an ethanolic solution containing 8% water.

44. The soft gelatin capsule of either paragraphs 42 or 43, further comprising a carrier.

45. The soft gelatin capsule of paragraph 44, wherein the carrier is DHLA.

46. The soft gelatin capsule of paragraph 44, wherein the carrier is a vegetable oil, a fish oil or a combination thereof.

47. The soft gelatin capsule of any of paragraphs 42 through 46, further comprising a an antioxidant or an antioxidant enzyme.

48. The soft gelatin capsule of paragraph 47, wherein the antioxidant is vitamin E, a vitamin E derivative, vitamin C, a vitamin C derivative, probucol, lycopene, vitamin A, a carotenoid, vitamin B, vitamin B1, a vitamin B derivative, a flavonoid, a polyphenol, glutathione, pyrroloquinoline quinone, Pycnogenol, Flavangenol, selenium, a lipoic acid, a lipoic acid derivative, a carnitine (e.g., L-camitine) or mixtures thereof.

49. The soft gelatin capsule of paragraph 47, wherein the antioxidant enzyme is superoxide dismutase, glutathione peroxidase, glutathione-S-transferase, glutathione reductase, catalase and ascorbic acid peroxidase or mixtures thereof.

50. The soft gelatin capsule of any of paragraphs 42 through 49, wherein the pH range of The soft gelatin capsule is between about a pH of 6 and a pH of 3.

51. The soft gelatin capsule of paragraph 50, wherein the pH range is between about 5.5 and about 3.5.

52. The soft gelatin capsule of paragraph 51, wherein the pH range is between about 4 and about 3.5.

53. The soft gelatin capsule of paragraph 52, wherein the pH range is between about 3.9 to about 3.8.

54. The soft gelatin capsule of any of paragraphs 42 through 53, wherein the reduced form of CoQ-10 is present in an amount of about 98.5% by weight or greater.

55. The soft gelatin capsule of any of paragraphs 42 through 53, wherein essentially all of the CoQ-10 is present in the reduced form.

56. A process to prepare a reduced coenzyme Q-10 solution, comprising the step of:
contacting coenzyme Q-10 (CoQ-10) with a sufficient amount of dihydrolipoic acid (DHLA) to reduce the CoQ-10 to a reduced form of CoQ-10 in greater than about 95% by weight.

57. The process of paragraph 56, wherein excess DHLA is used, such that the DHLA is also a carrier.

58. The process of either paragraph 56 or 57, wherein the process is conducted at a pH of below about a pH of 6.

59. The process of either paragraph 56 or 57, wherein the process is conducted at a pH of below about a pH of 5.

60. A method to treat periodontal diseases, mitochondrial related diseases and disorders, Parkinson's disease, Prater-Willey syndrome, migraine headaches or headaches comprising the step of administering to the individual in need thereof, an effective amount of any of the compositions of paragraphs 1 through 55.

61. A method to prepare reduced coenzyme Q-10 comprising the step of contacting a molar excess of dihydrolipoic acid with a mole of coenzyme Q-10, wherein the composition does not include an ethanolic solution containing 8% water.

62. The composition of paragraph 2, wherein the carrier is a monocyclic terpene.

63. The composition of paragraph 62, wherein the monocyclic terpene includes limonene, ginger oil, lavandin oil, peppermint oil, camphor oil, geranium oil, orange oil, lemon oil, lavender oil, tea tree oil, rosemary oil or mixtures thereof.

In a particular embodiment, the antioxidants are a mixture of one or more of L-camitine, glutathione and VB1

The following examples are intended to be illustrative only and should not be considered limiting.

EXAMPLE 1

Dissolution and Reduction of CoQ10 by DHLA (Preparation of 13% Solution)

1.1 g (1.27 mmol) CoQ10 (in its oxidized form) were added to 7.1 g (34.1 mmol) DHLA. The mixture was stirred until a uniform solution was achieved. The solution was kept at 25° C. for 1 week, afterwards HPLC analysis (UV detector at 210 nm) was performed. The ratio of oxide form of CoQ10 (ubiquinone) and reduced form (ubiquinol form) of CoQ10 in the mixture was 1:5 to 98.5. The pH-value of the solution was about 3.80 (measured by Metrohm 827 pH Lab).

EXAMPLE 2

Protection of Reduced Coenzyme Q10 Against Re-Oxidation Under Storage Conditions 3 g (3.48 mmol) CoQ10 (oxidized form) were dissolved in 40 ml THF, and 0.32 g (8.65 mmol) $NaBH_4$ were added. The solution was kept at 30° C. for 1 hour. Under HPLC analysis (UV detector at 210 nm), the oxidized form of CoQ10 (ubiquinone) was not detected in the solution.

Afterwards 30 ml $CH_2Cl_2$ were added, and the organic layer was washed three times with 6 mol/L HCl, dried with anhydrous $Na_2SO_4$, and 8.1 g (38.9 mmol) DHLA were added. The solution was distilled under vacuum to remove the $CH_2Cl_2$ and THF. The residue solution was stored for 1 week. Under HPLC analysis (UV detector at 210 nm), it was found that no re-oxidation of the reduced CoQ10 occurred.

EXAMPLE 3

Dissolution of CoQ10 in DHLA; Temperature Dependence of the Solubility

Coenzyme Q10 was dissolved in DHLA at various temperatures. FIG. 1 exhibits the solubility of CoQ10 at various temperatures. The ordinate shows the percentage of dissolved CoQ10 in DHLA.

When a solution of reduced CoQ10 in DHLA is cooled, the reduced CoQ10 will sometimes precipitate. Upon re-heating the reduced form, CoQ10 is re-dissolved in DHLA. After repeating this cycle, the oxidized form of CoQ10 could not be detected.

HPLC analysis, furthermore, shows that a redox reaction takes place in the CoQ10-DHLA solution. In this regard, the amount of DHLA that is oxidized is equal to the amount of CoQ10 that is reduced.

EXAMPLE 4

Preparation of an 8% Solution of CoQ10 in DHLA 0.9 g (1.04 mmol) CoQ10 (oxidized form) were added to 11.09 g (53.3 mmol) DHLA, The mixture was stirred until a uniform solution was achieved. The solution was kept at 25° C. for 1 week, afterwards HPLC analysis (UV detector at 210 nm) was performed. The ratio of oxide form of CoQ10 and reduced form (ubiquinol form) of CoQ10 in the mixture is 1:5 to 98.5. The pH-value of the solution was about 3.80 to 3.90.

The solution was kept at room temperature for about 1 month with no change in the composition detected as determined by HPLC.

EXAMPLE 5

Analysis of the Transformation of DHLA to Lipoic Acid (LA) and Stability of Reduced Form of CoQ10 by HPLC Analytical Methods
Instruments and Material:
HPLC: Waters 600 pump with 717 plus autosampler and 2996 PDA detector
Balance: Sartorius BP 211D
Regents: Acetonitrile (HPLC grade, Fisher), Distilled water (Nestle), Methanol (Fisher, HPLC grade)
Standards: DHLA (89.3%), LA from Sigma, 99.0%, oxidized CoQ10 (98.5%)
HPLC Conditions
LA and DHLA:
Mobile phase: 0.03% $H_3PO_4$: Acetonitrile=60:40
Column: Agilent ellipse XDB-C18 (150 mm*4.6 mm, 5 µm)
Temperature: 30° C.
UV-detection: 220 nm
Injection volume: 10 µl
Flow rate: 1.0 ml/min
Reduced and Oxidized CoQ10:
Mobile phase: Methanol:Ethanol=75:25
Column: Waters Symmetry C18 (150 mm*4.6 mm, 5 µm)
Temperature: 30° C.
UV-detection: 210 nm
Injection volume: 2 µl
Flow rate: 1.0 ml/min
The samples were made by dissolving 50~100 mg CoQ10-DHLA solution in a 5 ml volumetric bottle with methanol/ethanol (50/50, v/v).

The results are listed in Table 1.

TABLE 1

The area % of LA and reduced CoQ10 vs. reaction time

| Time(hour) | LA | Reduced CoQ10 |
|---|---|---|
| 0.5 | 2.03 | 4.57 |
| 2.5 | 2.37 | |
| 6.5 | 3.39 | 21.53 |
| 21 | 6.91 | |
| 23 | 7.14 | 69.03 |
| 25 | 7.33 | 73.46 |
| 28 | 7.76 | 85.77 |
| 30 | 7.92 | 87.18 |
| 34 | 8.2 | |
| 49 | 8.51 | 94.43 |
| 52 | 8.63 | 96.82 |
| 56 | 8.12 | 97.24 |
| 70 | 7.36 | 97.44 |

Table 1 provides the respective area-% of the lipoic acid (LA) (as compared to DHLA) and of the reduced form of CoQ10 (as compared to the oxidized form of CoQ10) in the CoQ10-DHLA solution.

The results show that after about 52 hours, the oxidized CoQ10 was almost completely reduced by DHLA. At the first 40 hours the content of reduced CoQ10 increases very fast, then the reaction rate slows down.

When close to the end point of the reaction, the reduced CoQ10 is very sensitive to the air and can be easily re-oxidized, so the content of reduced CoQ10 remains at about 97~98%.

EXAMPLE 6

20 g CoQ10 (oxidized form) were added to 80 g DHLA. The mixture was slowly stirred and heated at 37° C., until the solid was fully dissolved. The reaction time until CoQ10 was totally dissolved was around 7 days. After sealing the container with the CoQ10/DHLA solution, the reduced form of CoQ10 remained stable for at least one month (reduced CoQ10 value of 97-98% or more via HPLC as described herein). The pH-value of the solution was about 3.80 to 3.90.

EXAMPLE 7

10 g CoQ10 (oxidized form) were added to 5 g DHLA. The mixture was stirred and heated to 50° C. until the solid was fully dissolved. The bottle containing the solution was sealed and kept at a temperature of 50° C. for 70 days. Afterwards, the ratio of the reduced form of CoQ10 (ubiquinol) and the oxide form of CoQ10 in the solution was found to be over 99:1 as determined by HPLC described herein. The pH-value of the solution was about 3.80 to 3.90.

EXAMPLE 8

1.1 g CoQ-10 was dissolved in 7.1 g DHLA at 25° C. The formation of a CoQ-10 radical was followed by UV spectrophotometrically. If the reaction would proceed via radicals, it is expected that the CoQ-10 radical would appear as a prominent band around 480 nm.

However, there was no indication of radical formation as evidenced by the lack of a band at 480 nm. (See FIG. 2) This suggests that the reduction of the CoQ-10 occurs via a 2-electron transfer reaction mechanism. This would appear logical as at the pH of the reaction (3.80-3.90) DHLA is not susceptible to radical formation, which would be a prerequisite for a radical reaction.

Figure 2:
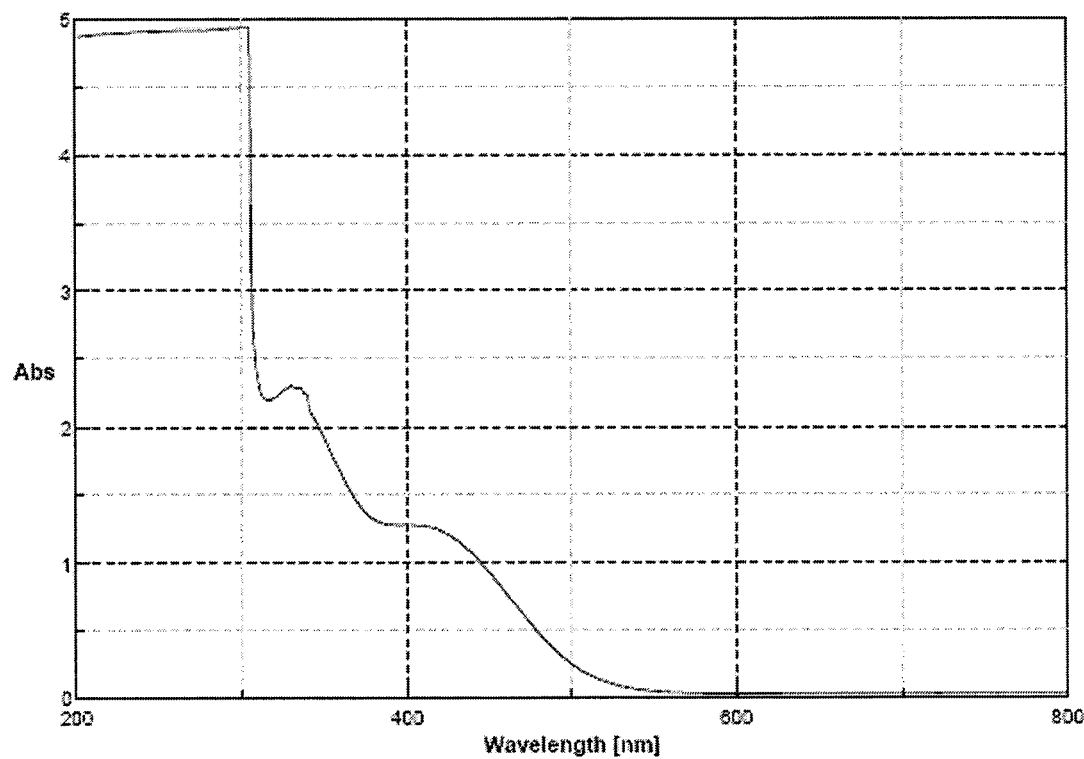
FIG. 2 is a UV spectrograph of the reaction between CoQ-10 and excess DHLA after 1 hour.

In FIG. 2, the band at approximately 320 nm indicates generation of lipoic acid (max. 320 nm) and a band at approximately 480 nm would be the region where a semiubiquinone radical would occur.

FIG. 2 was generated 1-hour post initiation of the reaction: As seen, lipoic acid is formed, but there is no indication of a ubiquinone radical.

Figure 3:
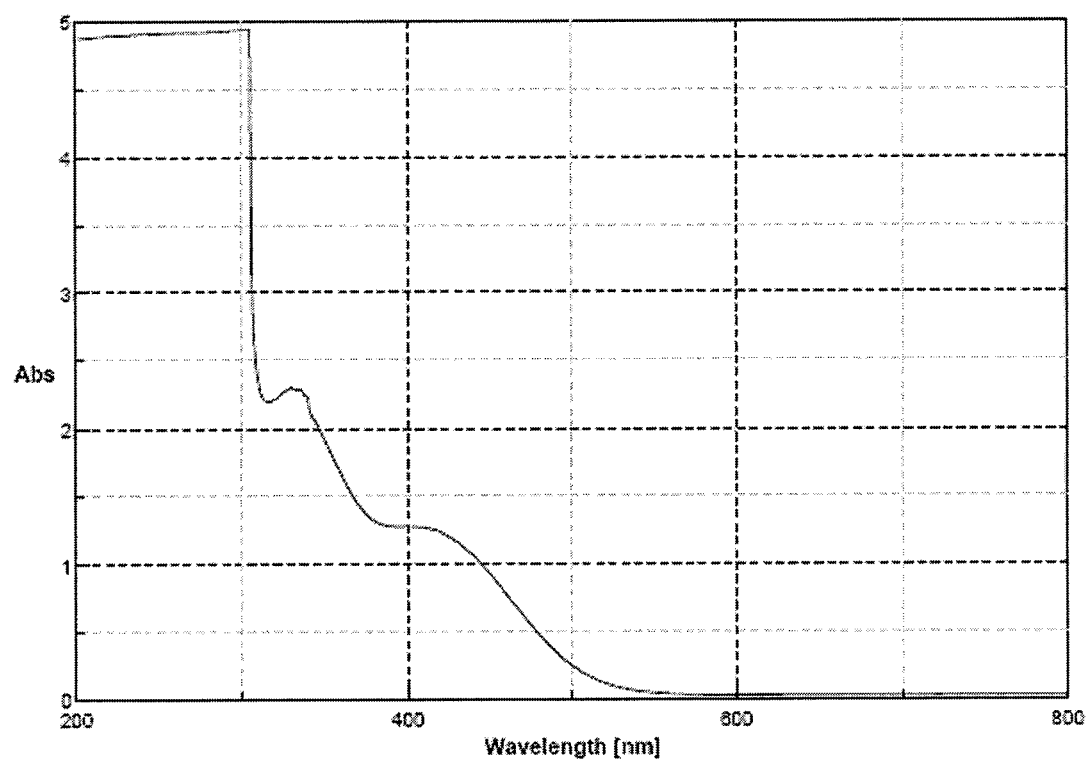
FIG. 3 is a UV spectrograph of the reaction between CoQ-10 and excess DHLA after 6 hours.

FIG. 3 was taken 6 hours post initiation. FIG. 3 demonstrates that there is no indication of a ubiquinone radical.

FIGS. 2 and 3 provide evidence that a 2-electron transfer reduction occurs between the components without radical formation.

EXAMPLE 9

Figure 4:
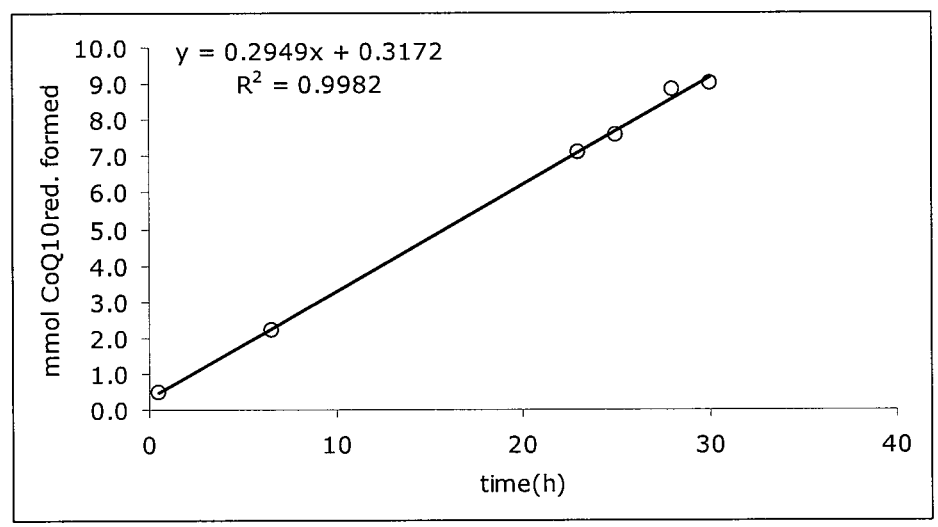
FIG. 4 is a graphical representation of the reduction of CoQ-10 with excess DHLA over a 30-hour time period.

The following example shows the time course of the reduction reaction between CoQ-10 and DHLA. As seen in FIG. 4, there is a linear relationship within the first 30 hours of reaction time, indicating that in a 8.9% CoQ10 solution (91.1% DHLA w/w, pH=about 3.8 to about 3.9, ambient temperatures), about 0.3 mmol reduced CoQ10/100 g solution are formed/hour.

The linear relationship noted in FIG. 4, also provides evidence for a non-radical reduction of CoQ-10.

What is interesting is that about 3 times more DHLA is oxidized (about 30 mmol) than are required for reduction of CoQ-10 (See Table 2). The most likely explanation is that equilibrium between DHLA/LA is reached on the basis of pK-values.

TABLE 2

| Reaction Time | mmol LA formed | mmol reduced CoQ10 formed |
|---|---|---|
| 0.5 | 9.0 | 0.47 |
| 2.5 | 10.5 | — |
| 6.5 | 15.0 | 2.22 |
| 21 | 30.6 | — |
| 23 | 31.6 | 7.12 |
| 25 | 32.4 | 7.58 |
| 28 | 34.3 | 8.85 |
| 30 | 35.0 | 8.99 |
| 34 | 36.3 | — |
| 49 | 37.6 | 9.74 |
| 52 | 38.2 | 9.98 |
| 56 | 35.9 | 10.03 |
| 70 | 32.5 | 10.05 |

Bioavailablity Testing

Material and Treatment:

Five male Sprague-Dawley rats (weighing 220-250 g, 7-8 weeks of age) can be used used in each treatment group. Treatment groups would include three groups. Group A would be with coenzyme Q10 with DHLA; Group B is with coenzyme Q10 with ascorbyl palmitate; and Group C would be with only coenzyme Q10. Rats would be dosed orally with coenzyme Q10 samples and the coenzyme Q10 dosage would be 20 mg/Kg.

The coenzyme Q10 with DHLA would be from the example 6 (Q10/DHLA=1/4, w/w);

The coenzyme Q10 plus ascorbyl palmitate, would be prepared with coenzyme Q10/ascorbyl palmitate=1/4, w/w, emulsified with a suitable emulsifying agent, such as a Tween;

Coenzyme Q10 would the reduced form of coenzyme Q10 without other functional agents.

Method and Detection:

Blood sampling (0.5 mL) would be taken after dosing (t=0) and 10, 20, 30, 40, 50, 60, 90, 120, 150, 180, 240 minutes after dosing.

An HPLC assay, measuring at 210 nm, would be used to detect for the quantity of reduced coenzyme Q10 in blood samples.

Analysis Method:

The mean reduced coenzyme Q10 plasma concentration of samples versus time after a single oral dose would be compared.

Expected Results:

The results should be that the reduced coenzyme Q10 plasma concentration of Group A is several times higher than that of Group B, and the coenzyme Q10 plasma concentration of Group C would be very low.

Conclusion:

Data obtained from the rats given oral administration of coenzyme Q10 can reveal coenzyme Q10 with DHLA was best absorbed with the best protection of reduced Q10 as well as the best retention of reduced coenzyme Q10 in vivo.

These results would account or the better bioavailability of the DHLA/reduced coenzyme Q10 product of the present invention.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

We claim:

1. A ubiquinol composition consisting of ubiquinol and glutathione fully dissolved in dihydrolipoic acid.

2. The composition of claim 1, wherein the composition is encapsulated within a soft gelatin capsule.

3. A ubiquinol composition, consisting of ubiquinol fully dissolved in dihydrolipoic acid.

* * * * *